United States Patent
Best et al.

(10) Patent No.: US 10,765,419 B2
(45) Date of Patent: Sep. 8, 2020

(54) ACTIVE DEPLOYING SOFT ANCHOR

(71) Applicant: Arthrex, Inc., Naples, FL (US)

(72) Inventors: Joshua J. Best, Naples, FL (US); John P. Gualdoni, Naples, FL (US); Tara L. Swanlaw, Estero, FL (US); Bryan T. Kelly, Riverside, CT (US)

(73) Assignee: Arthrex, Inc., Naples, FL (US)

( * ) Notice: Subject to any disclaimer, the term of this patent is extended or adjusted under 35 U.S.C. 154(b) by 219 days.

(21) Appl. No.: 15/885,170

(22) Filed: Jan. 31, 2018

(65) Prior Publication Data

US 2019/0231338 A1  Aug. 1, 2019

(51) Int. Cl.
*A61B 17/04* (2006.01)
*A61B 17/06* (2006.01)
*A61B 17/34* (2006.01)

(52) U.S. Cl.
CPC ...... *A61B 17/0401* (2013.01); *A61B 17/3401* (2013.01); *A61B 2017/0406* (2013.01); *A61B 2017/0409* (2013.01); *A61B 2017/0412* (2013.01); *A61B 2017/0414* (2013.01); *A61B 2017/0427* (2013.01); *A61B 2017/0464* (2013.01); *A61B 2017/06052* (2013.01); *A61B 2017/06185* (2013.01)

(58) Field of Classification Search
CPC ............ A61B 17/0487; A61B 17/0401; A61B 2017/0487; A61B 2017/0496; A61B 2017/0406; A61B 2017/0458; A61B 2017/0414
See application file for complete search history.

(56) References Cited

U.S. PATENT DOCUMENTS

| | | | |
|---|---|---|---|
| 9,320,512 B2 | 4/2016 | Dooney, Jr. | |
| 9,345,567 B2 | 5/2016 | Sengun | |
| 9,357,992 B2 | 6/2016 | Stone et al. | |
| 9,463,011 B2 | 10/2016 | Dreyfuss et al. | |
| 9,486,202 B2 | 11/2016 | Ferguson | |
| 9,622,738 B2 | 4/2017 | Dreyfuss et al. | |
| 9,724,090 B2 | 8/2017 | Kaiser et al. | |
| 2007/0185532 A1* | 8/2007 | Stone ................. | A61B 17/0482 606/232 |
| 2008/0065114 A1 | 3/2008 | Stone et al. | |
| 2009/0318961 A1* | 12/2009 | Stone .................... | A61F 2/0811 606/228 |
| 2011/0022083 A1* | 1/2011 | DiMatteo ........... | A61B 17/0401 606/228 |
| 2011/0098727 A1* | 4/2011 | Kaiser ................ | A61B 17/0401 606/144 |
| 2012/0024134 A1* | 2/2012 | Dow ....................... | D04C 7/00 87/8 |
| 2012/0046693 A1 | 2/2012 | Denham et al. | |
| 2012/0239085 A1* | 9/2012 | Schlotterback ........ | A61B 17/04 606/228 |
| 2012/0290004 A1 | 11/2012 | Lombardo et al. | |
| 2013/0131722 A1* | 5/2013 | Marchand .......... | A61B 17/0401 606/232 |
| 2014/0277133 A1 | 9/2014 | Foerster | |
| 2015/0127049 A1* | 5/2015 | Marchand .......... | A61B 17/0401 606/232 |
| 2016/0081789 A1 | 3/2016 | Denham et al. | |
| 2016/0157844 A1 | 6/2016 | Guy | |
| 2016/0287243 A1 | 10/2016 | Benedict et al. | |

* cited by examiner

*Primary Examiner* — Alexander J Orkin
(74) *Attorney, Agent, or Firm* — Blank Rome LLP

(57) ABSTRACT

A soft anchor, anchor assembly, and methods of inserting soft anchors into bone are disclosed herein.

16 Claims, 7 Drawing Sheets

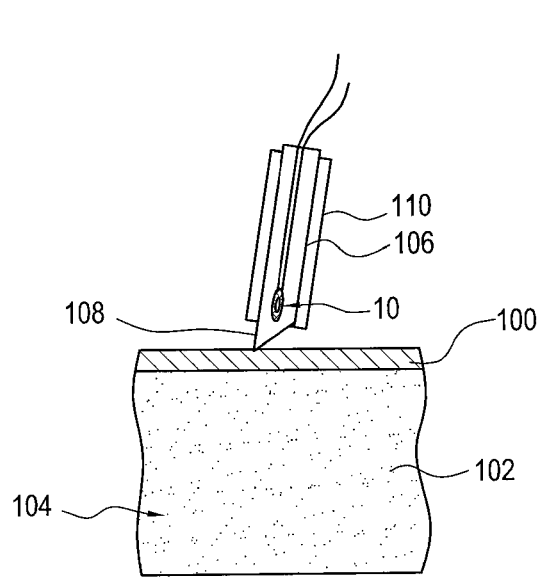 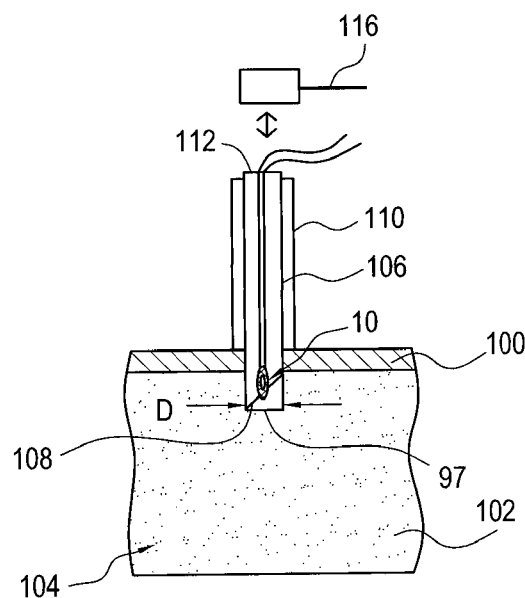
FIG. 13     FIG. 14
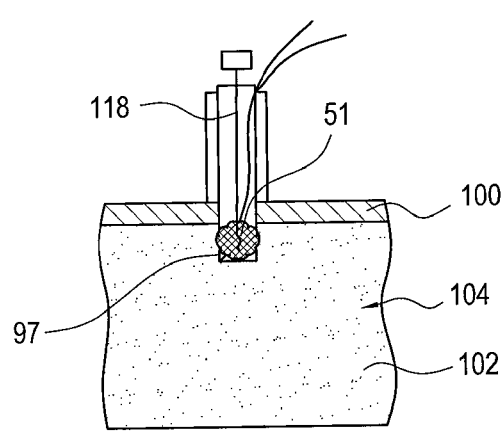 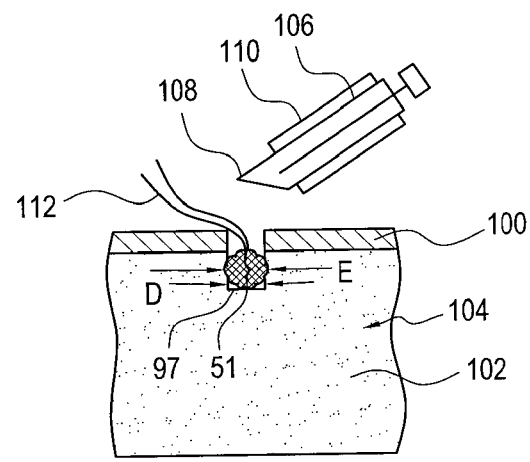
FIG. 15     FIG. 16

ACTIVE DEPLOYING SOFT ANCHOR

BACKGROUND

This disclosure relates to soft anchors for tissue fixation, anchor assemblies, and methods of inserting soft anchors into bone.

SUMMARY

A soft anchor secures soft tissue to bone. A soft anchor includes a sheath and a flexible strand located in a lumen defined by the sheath. The soft anchor is positioned in a hole in a bone in a non-deployed condition. When the flexible strand is tensioned, the sheath gathers around the flexible strand, and the soft anchor is in a deployed condition to secure the soft anchor within the hole in the bone.

Embodiments of a soft anchor disclosed herein include a soft anchor including a bifurcated sheath that defines a lumen and a deployable loop. A flexible strand is received in the lumen and the loop. In a non-deployed condition, there is no tension in the loop. The soft anchor is installed in a hole in a bone, the hole having a first dimension. When the flexible strand is pulled, the loop gathers around the flexible strand to form a sheath bundle having a second dimension greater than the first dimension to secure the soft anchor in the hole in the bone.

In an embodiment, a soft anchor includes a sheath having a lumen where the sheath includes at least one bifurcation that bifurcates the sheath into a first portion and a second portion at a distal end of the lumen. The soft anchor includes a flexible strand received in the sheath, the flexible strand including a first segment, a second segment, and a loop segment located therebetween. The first segment of the flexible strand passes through the lumen, the loop segment passes through the first portion and the second portion of the sheath, and the second segment of the flexible strand passes through the lumen. Portions of the first segment and the second segment of the flexible strand extend from a proximal end of the soft anchor.

In another embodiment, a soft anchor assembly includes a cannulated instrument and a sheath including a lumen that has at least one bifurcation that bifurcates the lumen into a first portion and a second portion at a distal end of the lumen. The soft anchor assembly includes a flexible strand received in the sheath, the flexible strand including a first segment, a second segment, and a loop segment located therebetween. The first segment of the flexible strand passes through the lumen, the loop segment passes through the first portion and the second portion of the sheath, and the second segment of the flexible strand passes through the lumen. Portions of the first segment and the second segment of the flexible strand extend from a proximal end of the soft anchor.

In another embodiment, a method of installing a soft anchor into bone comprises forming a hole in the bone; inserting the soft anchor into the hole, the soft anchor comprising a sheath and a flexible strand received in the sheath, the flexible strand including a first segment, a second segment, and a loop segment located therebetween, wherein the first and second segments of the flexible strand pass through a lumen of the sheath and the loop segment passes through bifurcated first and second portions of the sheath; and pulling portions of the flexible strand that extend outside of the sheath to gather the sheath around the loop segment of the flexible strand to form a sheath bundle to secure the soft anchor to the bone in the hole.

In yet another embodiment, a method of installing a soft anchor into bone includes positioning a cannulated instrument, such as a cannulated needle, on a bone, and a soft anchor is received in the cannulated needle. The cannulated needle may be received in a cannulated guide. The method includes forming a hole in the bone by moving the cannulated needle relative to the cannulated guide to locate a tip of the cannulated needle in the bone to form a hole, and the hole has a first dimension. The method includes pulling portions of a flexible strand of a soft anchor. The soft anchor includes a sheath including a lumen that bifurcates into a first portion and a second portion at a distal end of the lumen and the flexible strand is received in the sheath. The flexible strand includes a first segment, a second segment, and a loop segment located therebetween. The first segment of the flexible strand passes through the lumen, the loop segment passes through the first portion and the second portion of the sheath, and the second segment of the flexible strand passes through the lumen. The portions of the first segment and the second segment of the flexible strand extend from a proximal end of the soft anchor. The method includes gathering the sheath around the loop segment of the flexible strand to form a sheath bundle having a second dimension greater than the first dimension of the hole of the bone to secure the soft anchor to the bone.

BRIEF DESCRIPTION OF THE DRAWINGS

FIG. 13 is a schematic view of the soft anchor assembly of FIG. 12 aligned with a bone;

FIG. 14 is a schematic view of the soft anchor assembly of FIG. 12 forming a hole in a bone;

FIG. 15 is a schematic view of the soft anchor assembly of FIG. 12 installing a soft anchor in the hole in the bone; and FIG. 16 is a schematic view of the soft anchor assembly of FIG. 12 with the soft anchor received in the hole in the bone.

DETAILED DESCRIPTION

Figure 1:
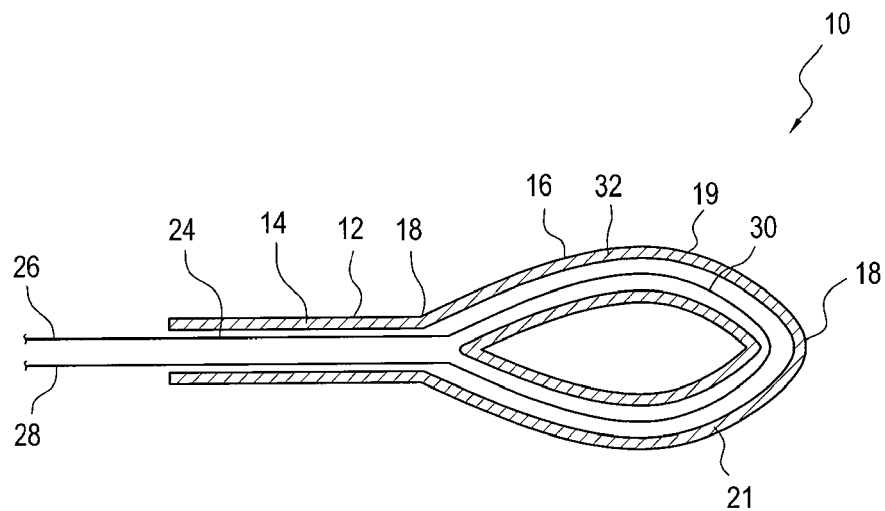
FIG. 1 is a schematic view of an embodiment of a soft anchor in a non-deployed condition.

Referring to the figures, the present disclosure generally relates to a soft anchor for securing soft tissue to bone. A soft anchor includes a sheath and a flexible strand located in a lumen defined by the sheath. The soft anchor is positioned in a hole in a bone in a non-deployed condition. When the flexible strand is tensioned, the sheath gathers around the flexible strand, and the soft anchor is in a deployed condition to secure the soft anchor within the hole in the bone.

Embodiments of a soft anchor disclosed herein include a soft anchor including a bifurcated sheath that defines a lumen and a deployable loop. At least one flexible strand is received in the lumen and the loop. In a non-deployed condition, there is no tension in the loop. The soft anchor is installed in a hole in a bone, the hole having a first dimension. When the flexible strand is pulled, the loop gathers around the flexible strand to form a sheath bundle having a second dimension greater than the first dimension to secure the soft anchor in the hole in the bone.

In an embodiment, a soft anchor includes a sheath including a lumen and at least one bifurcation that bifurcates the sheath into a first portion and a second portion at a distal end thereof. The soft anchor includes a flexible strand received in the sheath, the flexible strand including a first segment, a second segment, and a loop segment located therebetween. The first segment of the flexible strand passes through the lumen, the loop segment passes through the first portion and the second portion of the sheath, and the second segment of the flexible strand passes through the lumen. Portions of the first segment and the second segment of the flexible strand extend from a proximal end of the soft anchor outside of the sheath.

In an embodiment, the first portion and the second portion of the sheath are connected to form a sheath loop. In an embodiment, the first portion and the second portion of the sheath are connected by a stitch. In an embodiment, the sheath includes barbs on an external surface of the sheath. In an embodiment, the sheath includes another bifurcation at a proximal end of the lumen that bifurcates the sheath into at least two portions. In an embodiment, the flexible strand is not tensioned when the soft anchor is in a non-deployed condition, and when the soft anchor is in a deployed condition, the flexible strand is tensioned to gather the sheath around the flexible strand loop segment to form a sheath bundle, and a dimension of the sheath bundle is greater than a hole in a bone that receives the soft anchor.

In another embodiment, a soft anchor assembly includes an instrument, such as a cannulated instrument or forked instrument, and a sheath including a lumen that bifurcates into a first portion and a second portion at a distal end of the lumen. The soft anchor assembly includes a flexible strand received in the sheath, the flexible strand including a first segment, a second segment, and a loop segment located therebetween. The first segment of the flexible strand passes through the lumen, the loop segment passes through the first portion and the second portion of the sheath, and the second segment of the flexible strand passes through the lumen with the first segment. Portions of the first segment and the second segment of the flexible strand extend from a proximal end of the soft anchor.

In another embodiment, the instrument is received in an outer cannula. In an embodiment, the first portion and the second portion of the sheath are connected to form a sheath loop. In an embodiment, the first portion and the second portion of the sheath are connected by a stitch. In an embodiment, the sheath includes barbs on an external surface of the sheath. In an embodiment, the sheath may also bifurcate at a proximal end of the lumen into at least two portions. In an embodiment, the flexible strand is not tensioned when the soft anchor is in a non-deployed condition, and when the soft anchor is in a deployed condition, the flexible strand is tensioned to reduce a length of the flexible strand at a distal end of the instrument and gather the sheath around the flexible strand loop segment to form a sheath bundle at the distal end of the instrument, and a dimension of the sheath bundle is greater than a hole in a bone that receives the soft anchor.

In a further embodiment, a method of installing a soft anchor into bone includes positioning a cannulated needle on a bone, and a soft anchor is received in the cannulated needle, and the cannulated needle is received in a cannulated guide. The method includes forming a hole in the bone by moving the cannulated needle relative to the cannulated guide to locate a tip of the cannulated needle in the bone to form a hole, and the hole has a first dimension. The method includes pulling portions of a flexible strand of a soft anchor. The soft anchor includes a sheath including a lumen that bifurcates into a first portion and a second portion at a distal end of the lumen, the flexible strand is received in the sheath. The flexible strand includes a first segment, a second segment, and a loop segment located therebetween. The first segment of the flexible strand passes through the lumen, the flexible strand loop segment passes through the first portion and the second portion of the sheath, and the second segment of the flexible strand passes through the lumen. The portions of the first segment and the second segment of the flexible strand extend from a proximal end of the soft anchor. The method includes gathering the sheath around the loop segment of the flexible strand to form a sheath bundle having a second dimension greater than the first dimension of the hole of the bone to secure the soft anchor to the bone. In an embodiment, a method comprises abutting a sheath against a distal end of an instrument that receives at least a portion of the lumen of the sheath when pulling the flexible strand and forming the sheath bundle.

In still another embodiment, the method includes moving the cannulated needle by impacting a proximal end of the needle with a mallet. In an embodiment, the method includes moving a pushrod towards the hole in the bone to insert the soft anchor into the hole. In an embodiment, the method includes removing the cannulated needle and the guide from the bone. In an embodiment, the method includes attaching soft tissue to the soft anchor.

FIG. 1 illustrates a soft anchor 10. The soft anchor 10 comprises a sheath 12 including a lumen 14 and a loop 16 configured to receive at least one flexible strand 24. The flexible strand 24 may be, for example, a suture, a plurality of sutures, wire, tape, or the like. In one exemplary embodiment, the sheath 12 is braided. The sheath 12 bifurcates to define a bifurcation at a first location 18 into two segments 19 and 21 and the two segments 19 and 21 reconnect at a second location 20 to define the loop 16. In one exemplary embodiment, the sheath 12 is joined at the second location 20 when the sheath 12 is formed. In another exemplary embodiment, the sheath 12 is joined at the second location 20 by a securing feature, such as by stitching. In another exemplary embodiment, the sheath 12 is not joined at the second location 20, allowing a portion of the flexible strand 24 to be exposed.

The flexible strand 24 is preferably routed through the sheath 12 and may be slidable with respect to the sheath. The flexible strand 24 includes a first portion 26 and a second portion 28 and a loop segment 30 defined therebetween. The first portion 26 of the flexible strand 24 extends through the lumen 14 of the sheath 12, the flexible strand 24 extends through the loop 16 of the sheath 12 to form the loop segment 30, and the second portion 28 of the flexible strand 24 extends through the lumen 14 of the sheath 12 with the first portion 26 such that both portions 26 and 28 are in the same lumen of the sheath 12. The ends of portions 26 and 28 of the flexible strand 24 may be located outside the sheath 12 of the soft anchor 10, such that both portions 26 and 28 extend from a proximal end 23 of the sheath 12 that is remote from the sheath's loop 16.

In one exemplary embodiment, the sheath 12 includes one or more barbs 32 on an external surface thereof to increase friction between the soft anchor 10 and bone when the soft anchor 10 is installed or inserted into the hole in the bone. In one exemplary embodiment, the barbs 32 are formed on the sheath 12 using a hot loop to melt the sheath 12 to form the barbs 32. In another exemplary embodiment, the barbs 32 are formed on the sheath 12 using a laser.

Figure 2:
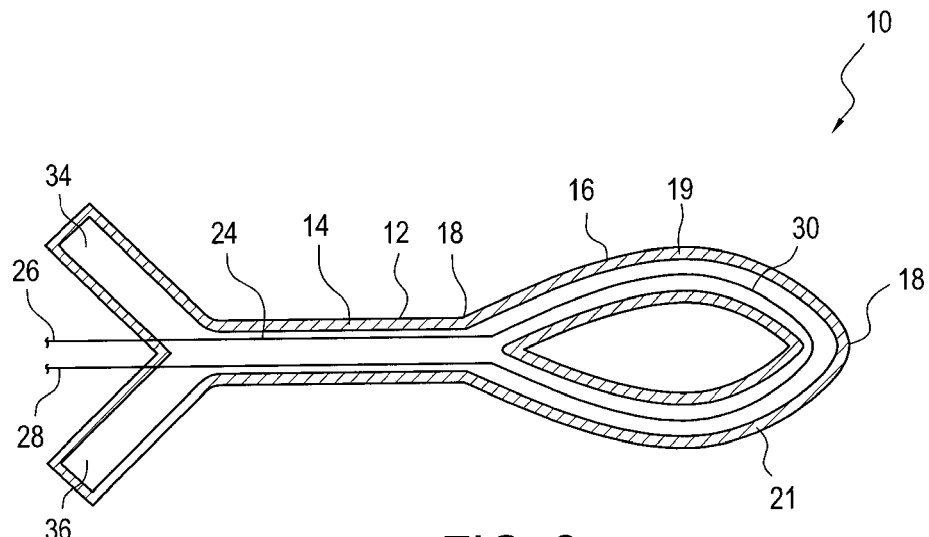
FIG. 2 is a schematic view of an embodiment of a soft anchor in the non-deployed condition.

In another exemplary embodiment shown in FIG. 2, the sheath 12 may also have a bifurcation at its proximal end 23 in which sheath 12 bifurcates into at least two segments 34 and 36 at its proximal end 23. This creates more bunching faster when tension is put onto strand portions 26 and 28. Portions 26 and 28 may extend through the segments 34 and 36, respectively, or may extend through an opening at the end of the bifurcation, to create the bunching effect.

Figure 3:
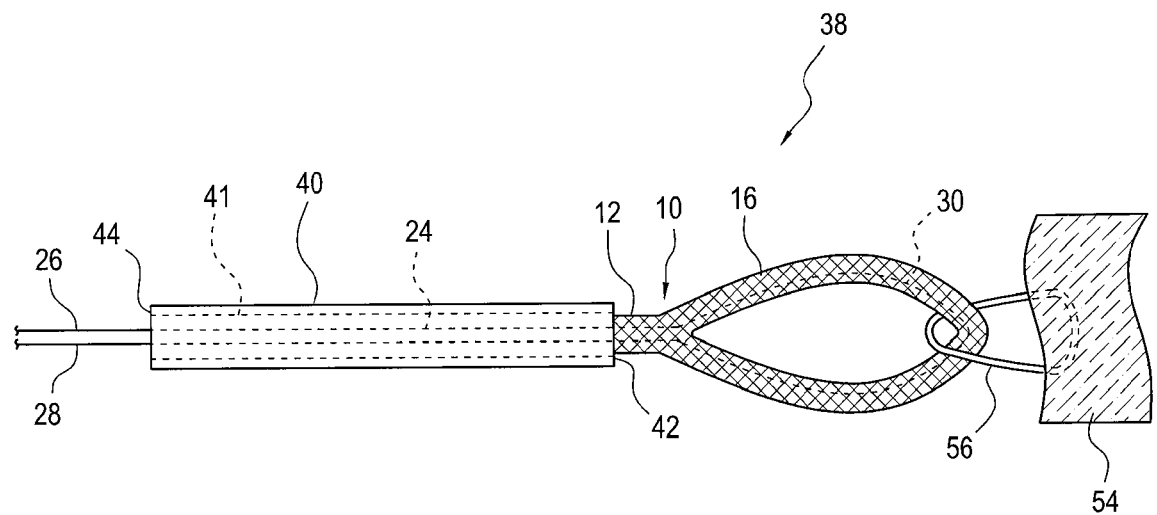
FIG. 3 is a schematic view of an embodiment of a soft anchor assembly including a soft anchor in a non-deployed condition, the soft anchor connected to soft tissue.

FIG. 3 illustrates a soft anchor assembly 38 including the soft anchor 10 in a non-deployed condition. The sheath 12 and a portion of the flexible strand 24 of the soft anchor 10 are received in an instrument, such as a cannulated instrument 40 having a passage 41. Alternatively, the instrument may be a forked instrument in which the soft anchor 10 is received in the fork of the forked instruction. The flexible strand loop segment 30 extends from a distal end 42 of the cannulated instrument 40, and a segment of the portions 26 and 28 of the flexible strand 24 extend from the proximal end 44 of the cannulated instrument 40. When the soft anchor 10 is in the non-deployed condition, there is no tension in the flexible strand loop segment 30, and the flexible strand 24 is generally loose. The loop 16 of the sheath 12 and the flexible strand loop segment 30 are preferably flexible. The soft anchor 10 is attached to soft tissue 54 with a flexible strand 56 where the flexible strand preferably extends through the loop 16 of anchor 10 or knotted with portions 26 and 28 and extends through or around the tissue 54.

Figure 4:
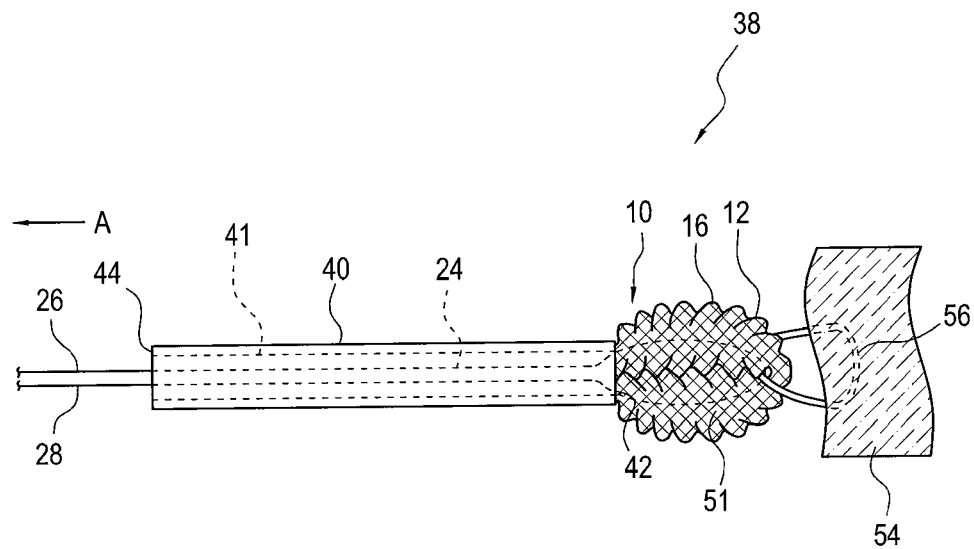
FIG. 4 is a schematic view of an embodiment of the soft anchor assembly of FIG. 3 in a deployed condition.

As shown in FIG. 4, when the portions 26 and 28 of the flexible strand 24 are pulled proximally in a direction A away from loop 16, the loop segment 30 of the flexible strand 24 pulls the sheath in the direction A, thereby bunching the sheath 12 at the end distal end 42 of the instrument 40, thereby creating a sheath bundle 51. As the loop 16 of the sheath 12 is located outside the cannulated instrument 40 and has a larger diameter than a passage 41 of the cannulated instrument 40, the pulling of portions 26 and 28 of the flexible strand 24 causes the sheath 12 to gather at the distal end 42 of the cannulated instrument 40 and form the sheath bundle 51. Alternatively, the sheath bundle can be created manually such as by inserting it on a fork.

Figure 5:
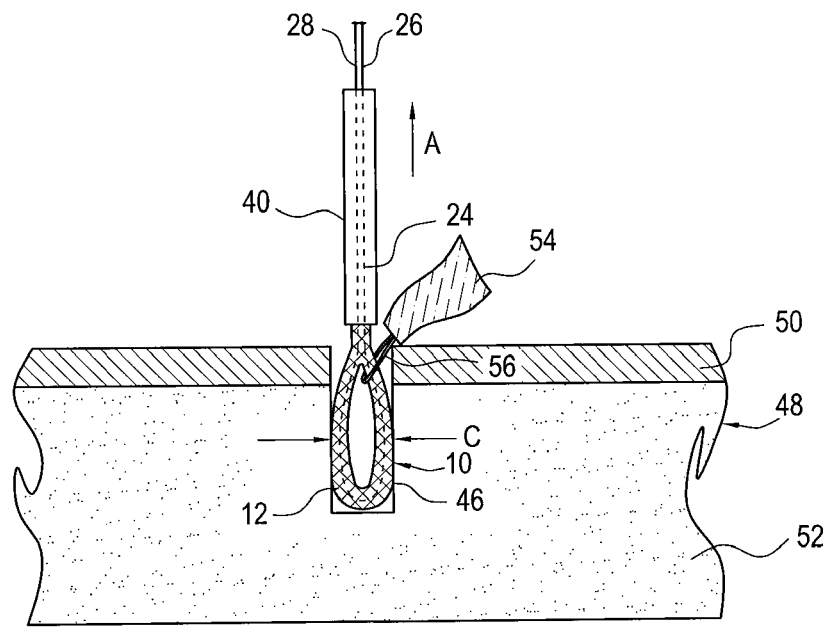
FIG. 5 is a schematic view of a soft anchor inserted into a hole in a bone in the non-deployed condition.

FIG. 5 illustrates installation of the soft anchor 10 in a hole 46 in a bone 48. First, the hole 46 is drilled in the bone 48, the bone 48 including a cortical layer 50 and soft cancellous bone tissue 52. The hole 46 has a dimension C. Next, the flexible strand 56 is threaded through the soft tissue 54 and through the loop 16 of the sheath 12 of the soft anchor 10 to secure the soft tissue 54 to the soft anchor 10. This may be done prior to inserting the anchor into the bone hole 46. The soft anchor 10 in the non-deployed condition is then installed into the hole 46 in the bone 48 using the cannulated instrument 40. In the non-deployed condition, the flexible strand 24 is not tensioned.

Figure 6:
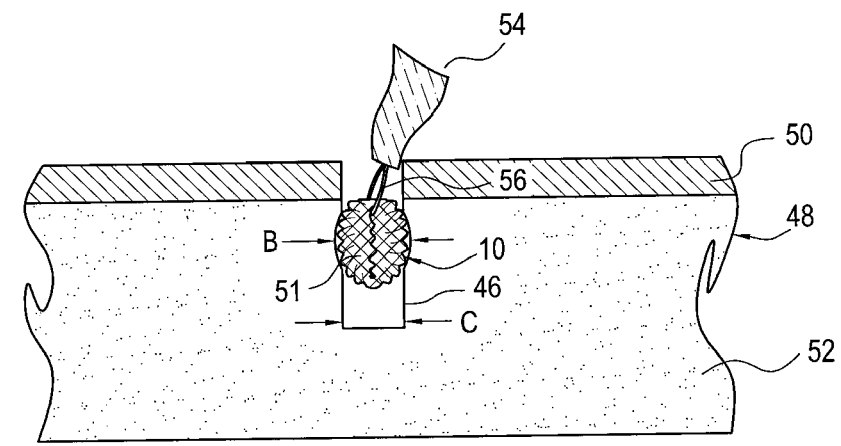
FIG. 6 is a schematic view of the soft anchor of FIG. 5 in the deployed condition.

Once the soft anchor 10 is received in the hole 46 in the bone 48, the portions 26 and 28 of the flexible strand 24 are pulled in the direction A to tension the flexible strand 24 and gather the sheath 12 at the distal end 42 of the cannulated instrument 40 to form the sheath bundle 51, as shown in FIG. 6, such that the soft anchor 10 is in the deployed condition.

The sheath bundle 51 has a dimension B. As the dimension B of the sheath bundle 51 is greater than the dimension C of the hole 46 in the bone 48, the soft anchor 10 presses against the soft cancellous bone tissue 52 surrounding the hole 46 to secure the soft anchor 10 to the bone 48 and secure the soft tissue 54 to the bone 48. The sheath 12 locks the shape of gathered sheath bundle 51 to secure the soft anchor 10 to the bone 48. Barbs 32 may also assist in securing the soft anchor 10 in the hole 46 in the bone 48. In one exemplary embodiment, the portions 26 and 28 of the flexible strand 24 may be knotted around the tissue 54 to maintain the soft anchor 10 in the deployed condition. In another exemplary embodiment, a wedge element may be wedged between the sheath 12 and the bone 48 to lock the anchor 10 in the deployed condition.

Figure 7:
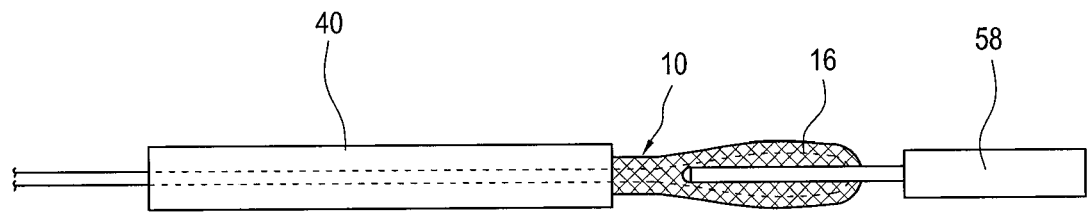
FIG. 7 is a schematic view of a loop of a soft anchor grasped by an instrument.

In another exemplary embodiment shown in FIG. 7, the loop 16 of the sheath 12 of the soft anchor 10 is adapted to be grasped by a pulling instrument 58 that pulls the soft anchor 10, including the loop 16, through a guide member, such as a drill guide, to facilitate implantation of the soft anchor 10 in the hole 46. The pulling instrument 58 may be a forked grasper or the like, for example.

Figure 8:
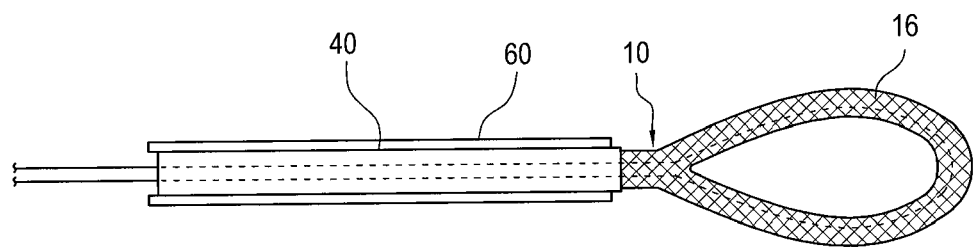
FIG. 8 is a schematic view of an instrument including an outer cannula.

In another exemplary embodiment shown in FIG. 8, the cannulated instrument 40 further includes an outer cannula 60. The flexible strand 24 is tensioned inside the cannulated instrument 40 as described above and the outer cannula 60 protects the soft anchor 10 when in the deployed condition to form the sheath bundle 51. That is the outer cannula 60 has a diameter greater than the diameter B (FIG. 6) of the sheath bundle such that the outer cannula can cover the sheath bundle 51 when the flexible strand 24 is tensioned and the soft anchor 10 is deployed.

Figure 9:
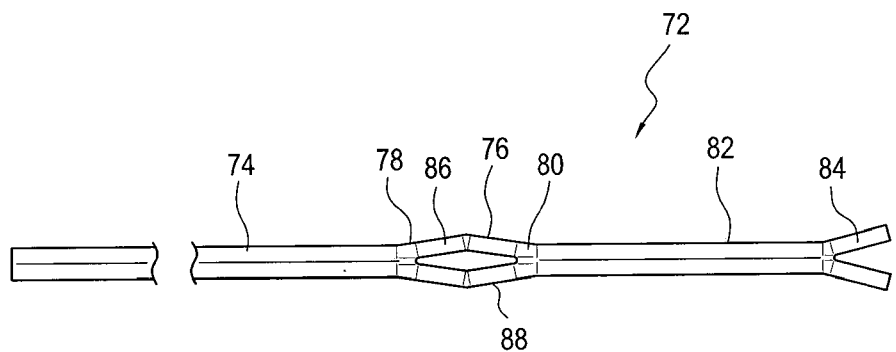
FIG. 9 is a schematic view of an embodiment of the soft anchor including a bifurcated sheath.
Figure 10:
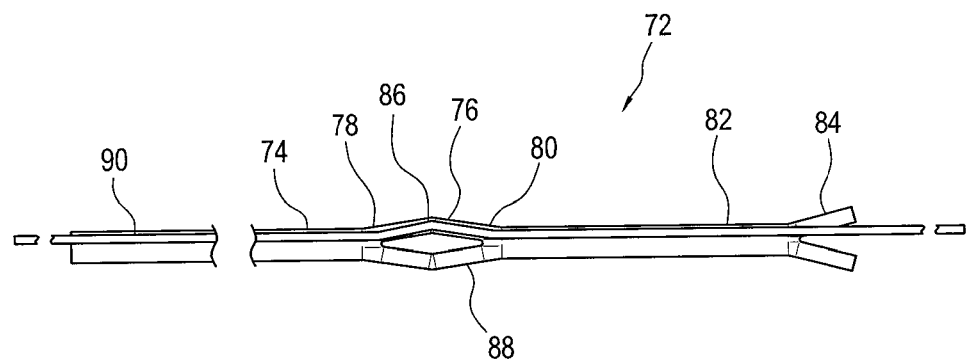
FIG. 10 is a schematic view of the soft anchor of FIG. 9 with a flexible strand threaded through the bifurcated sheath.
Figure 11:
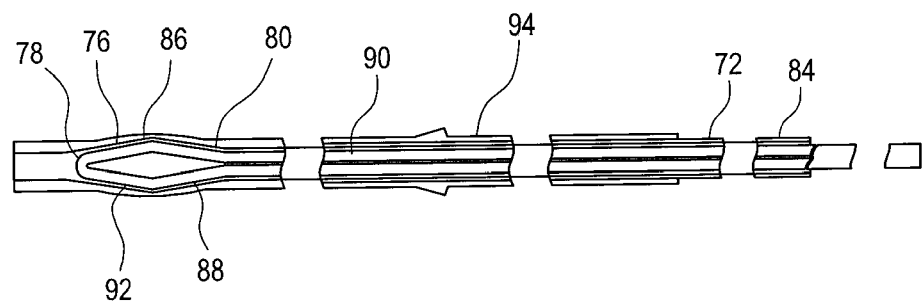
FIG. 11 is a schematic view of the soft anchor of FIG. 10 with the soft anchor inserted in a deployment tube.

FIGS. 9 to 11 illustrate another exemplary embodiment of an active deploying soft anchor 70. FIG. 9 illustrates a bifurcated sheath 72. In one exemplary embodiment, the sheath 72 is braided. A first portion 74 of the sheath 72 may be tapered and may include extra length which can be later removed during manufacturing. The taper of the first portion can be produced manually or by removing or cutting off a portion of the sheath 72. A second middle portion 76 of the sheath 72 may have a bifurcation at a location 78, thereby defining a first passage 86 and a second passage 88, and then reconnects at a location 80. A third portion 82 of the sheath 72 may include another bifurcation which bifurcates the sheath into at least two segments 84. Portions of the strand may extend through segments 84, respectively, or through an opening at the end of the bifurcation, to create the bunching effect.

As shown in FIGS. 10 and 11, a flexible strand 90 is threaded through the third portion 82 of the sheath 72, passes through one of the passages 86 and 88 of the second middle portion 76, through the tapered first portion 74, passes back through the other of the passages 86 and 88 of the second middle portion 76, and passes through the third portion 82 to exit the sheath 72 at the segments 84.

A portion of the flexible strand 90 remaining near the first portion 74 is threaded through the lumen of the first portion 74, passes through the other passage 88 of the bifurcated middle portion 76, and passes through the third portion 82 to exit the another bifurcated segment 84. The flexible strand 90 forms a loop segment 92 at the bifurcated middle portion 76 (shown in FIG. 11).

As shown in FIG. 11, the soft anchor 70 is then installed in a deployment tube 94. A passing flexible strand or pulling instrument may be attached near a tip of the first portion 74 to pull the soft anchor 70 into a deployment tube 94. This tube 94 may be inserted into the bone hole. In one exemplary embodiment, the passing flexible strand is attached approximately 3 mm from the tip of the first portion 74. An instrument, such as blunt tip needle, can be used to compress the sheath 72 into the deployment tube 94.

Once the soft anchor 70 is installed into the deployment tube 94, any extra material at the tapered first portion 74 of the sheath 72 can be removed. The soft anchor 70 is then installed and can be deployed in the same manner as described above.

Figure 12:
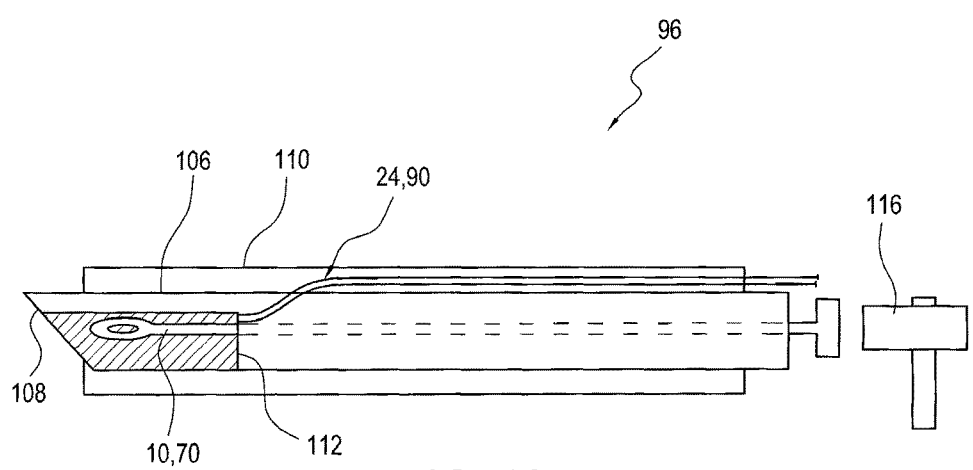
FIG. 12 is a schematic view of an embodiment of a soft anchor assembly.

FIG. 12 illustrates a self punching insertion delivery system 96 that can be used to create a hole 97 in a cortical layer 100 and soft cancellous bone tissue 102 of bone 104 and to install a soft anchor, such as soft anchor 10 described above, in the hole 97. In FIG. 12, the soft anchor 10 is in its non-deployed condition. The soft anchor 10 is preferably located inside a cannulated needle 106 that has a sharp or pointed tip 108 at a distal end thereof. The needle 106 may be received in a cannulated drill guide 110. Segments of a flexible strand, such as strand 24 described above, of the soft anchor 10 extend out of a proximal end of the soft anchor 10, out of a proximal end 112 of the needle 106, and out a proximal end 114 of the cannulated drill guide 110.

As shown in FIG. 13, the tip 108 of the needle 106 is received in the cannulated drill guide 110 and aligned with a desired location on the bone 104. A mallet 116, as shown in FIG. 14, impacts the proximal end 112 of the needle 106 to push the tip 108 of the needle 106 into the bone 104 to create the hole 97 in the bone 104. The hole 97 has a dimension D. In an alternative embodiment, an obturator may be used that supports the drill guide 110 during introduction and impaction of the needle 106 with the bone 104 when creating the hole 97.

As shown in FIG. 15, once the hole 97 is created by the needle 106, a pushrod 118 (shown in dashed lines in FIG. 12) located inside the cannulated needle 106 engages the soft anchor 10 to push the soft anchor 10 distally while the segments of the flexible strand 24, that extend out of the proximal end of the soft anchor 10, are pulled proximally away from the needle's tip 108, thereby tensioning the flexible strand 24 at the distal end of the needle 106 and moving the soft anchor 10 beyond the tip 108 of the needle 106. As the flexible strand 24 is pulled, a sheath bundle is gathered and formed within the hole 97 in the bone 104 such that the soft anchor 10 is in its deployed condition. When in the deployed condition, the sheath bundle 51 of the soft anchor 10 has a dimension B greater than the dimension D of the hole 97. As shown in FIG. 16, the needle 106, the cannulated drill guide 110, and the pushrod 118 may all be removed, thereby leaving the deployed soft anchor 10 inside the hole 97 of the bone 104.

The foregoing description is only exemplary of the principles of the disclosed subject matter. Many modifications and variations are possible in light of the above teachings.

What is claimed is:

1. A soft anchor, comprising:
    a single one-piece sheath including opposite distal and proximal ends, a lumen having a length that forms a longitudinal portion of the sheath, and at least one bifurcation bifurcating the sheath into first and second bifurcated portions at or near the distal end of the sheath, such that the bifurcation is located between the lumen and the first and second bifurcated portions; and
    at least one flexible strand received in the sheath, the at least one flexible strand including a first segment, a second segment, and a loop segment located therebetween, wherein the first segment passes through the length of the lumen, the loop segment continuously passes through respective passageways of the first and second bifurcated portions of the sheath, and the second segment passes through the length of the lumen with the first segment,
    wherein at least a portion of each of the first and second segments of the at least one flexible strand extends from the lumen at the proximal end of the sheath outside of the sheath and
    wherein the first and second bifurcated portions are connected to form a sheath loop at the distal end of the sheath, the sheath loop having a first dimension when the at least one flexible strand is not tensioned, the sheath loop having a second dimension greater than the first dimension when the at least one flexible strand is pulled to gather the sheath loop around the loop segment of the at least one flexible strand to form a sheath bundle.

2. The soft anchor as recited in claim 1, wherein the first bifurcated portion and the second bifurcated portion of the sheath are connected by stitching.

3. The soft anchor as recited in claim 1, wherein one or more barbs are located on an external surface of the sheath.

4. The soft anchor as recited in claim 1, wherein the sheath includes another bifurcation at the proximal end of the lumen such that the proximal end bifurcates into at least two portions.

5. A soft anchor assembly, comprising:
    an instrument;
    a single one-piece sheath including opposite distal and proximal ends, a lumen having a length that forms a longitudinal portion of the sheath, and at least one bifurcation bifurcating the sheath into first and second bifurcated portions at or near the distal end of the sheath, such that the bifurcation is located between the lumen and the first and second portions; and
    at least one flexible strand received in the sheath, the at least one flexible strand including a first segment, a second segment, and a loop segment located therebetween, wherein the first segment passes through the length of the lumen, the loop segment continuously passes through respective passageways of the first bifurcated portion and the second bifurcated portion of the sheath, and the second segment passes through length of the lumen with the first segment,
    wherein at least a portion of each of the first and second segments of the at least one flexible strand extends from the lumen at the proximal end of the sheath outside of the sheath and
    wherein the first and second bifurcated portions are connected to form a sheath loop at the distal end of the sheath, the sheath loop having a first dimension when the at least one flexible strand is not tensioned, the sheath loop having a second dimension greater than the first dimension when the at least one flexible strand is pulled to gather the sheath loop around the loop segment of the at least one flexible strand to form a sheath bundle.

6. The soft anchor assembly as recited in claim 5, wherein the instrument is a cannulated instrument.

7. The soft anchor assembly as recited in claim 5, wherein the first bifurcated portion and the second bifurcated portion of the sheath are connected by stitching.

8. The soft anchor assembly as recited in claim 5, wherein one or more barbs are located on an external surface of the sheath.

9. The soft anchor assembly as recited in claim 5, wherein the sheath includes another bifurcation at a proximal end of the lumen such that the proximal end bifurcates into at least two portions.

10. A method of installing a soft anchor into bone:
forming a hole in the bone;
inserting the soft anchor into the hole, the soft anchor comprising a sheath and a flexible strand received in the sheath, the flexible strand including a first segment, a second segment, and a loop segment located therebetween, wherein both the first and second segments of the flexible strand pass through a lumen of the sheath and the loop segment continuously passes through respective passageways of bifurcated first and second portions of the sheath wherein the first and second bifurcated portions are connected to form a sheath loop at a distal end of the sheath, the sheath loop having a first dimension when the at least one flexible strand is not tensioned; and
pulling portions of the flexible strand that extend outside of a proximal end of the sheath to gather the sheath around the loop segment of the flexible strand to form a sheath bundle to secure the soft anchor to the bone in the hole the sheath bundle has a second dimension greater than the first dimension.

11. The method as recited in claim 10, further comprising abutting the sheath against a distal end of an instrument when pulling the flexible strand and forming the sheath bundle.

12. The method as recited in claim 10, wherein the forming of the hole in the bone includes moving a cannulated needle that receives the soft anchor relative to a cannulated guide, which has the needle received therein, to locate a tip of the cannulated needle in the bone to form the hole.

13. The method as recited in claim 12, wherein the cannulated needle is moved by impacting a proximal end of the needle with a mallet.

14. The method as recited in claim 12, further comprising the step of moving a pushrod towards the hole in the bone to insert the soft anchor into the hole.

15. The method as recited in claim 12, further comprising the step of removing the cannulated needle and the guide from the bone.

16. The method as recited in claim 10, further comprising the step of attaching soft tissue to the sheath loop of the soft anchor.

* * * * *